United States Patent [19]

Ikarashi et al.

[11] 4,163,863
[45] Aug. 7, 1979

[54] PROCESS FOR PREPARING A METHYLPHENOL

[75] Inventors: Takeo Ikarashi, Niigata; Mikio Goto; Kozo Sano, both of Matsudo; Naoto Osaki, Tokyo; Tetsuo Aoyama, Niigata; Shigeru Horie, Tokyo, all of Japan

[73] Assignee: Mitsubishi Gas Chemical Company, Inc., Tokyo, Japan

[21] Appl. No.: 877,890

[22] Filed: Feb. 15, 1978

Related U.S. Application Data

[63] Continuation of Ser. No. 736,127, Oct. 27, 1976, abandoned.

[30] Foreign Application Priority Data

Nov. 4, 1975 [JP] Japan ................................. 50-132273

[51] Int. Cl.$^2$ ............................................. C07C 39/06
[52] U.S. Cl. .................................... 568/798; 568/569
[58] Field of Search ............................. 568/798, 799; 260/610 B

[56] References Cited

U.S. PATENT DOCUMENTS

| | | | |
|---|---|---|---|
| 2,750,424 | 6/1956 | Armstrong et al. | 568/798 |
| 3,293,308 | 12/1966 | Vol Epstein | 568/798 |
| 3,305,590 | 2/1969 | Pillin | 568/799 |

FOREIGN PATENT DOCUMENTS 1468895  1/1967  France ...................... 568/799

*Primary Examiner*—Werren B. Lone
*Attorney, Agent, or Firm*—Brooks, Haidt, Haffner & Delahunty

[57] ABSTRACT

A process for preparing a methylphenol from an alkylbenzene which process comprises oxidizing by molecular oxygen an alkylbenzene having one secondary alkyl group and 1–3 methyl groups of the general formula I

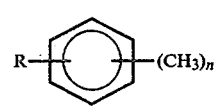

(I)

where R is a secondary alkyl group and n is an integer of 1–3, acid-decomposing the oxidation product solution in the presence of an acid catalyst, stopping the acid-decomposition reaction before its completion, hydrogenating the acid decomposition product solution in the presence of a hydrogenation catalyst in the presence or absence of a solvent, and recovering the resulting methylphenol of the general formula II

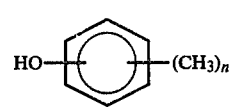

(II)

where n is an integer of 1–3 from the hydrogenation product solution.

14 Claims, 2 Drawing Figures

PROCESS FOR PREPARING A METHYLPHENOL

This application is a continuation of serial number 736,127, filed Oct. 27, 1976, now abandoned.

BACKGROUND OF THE INVENTION

1. Field of the Invention

This invention relates to a process for preparing a methylphenol, and more particularly, to a process for preparing a methylphenol by acid-decomposing the hydroperoxide obtained by oxidizing an alkylbenzene havine one secondary alkyl group and 1–3 methyl groups.

2. Description of the Prior Art

A process for preparing phenol by oxidizing cumene to the hydroperoxide, acid-decomposing the resulting hydroperoxide in the presence of an acid catalyst such as a mineral acid to produce phenol and acetone, neutralizing the acid catalyst and separating phenol and acetone by distillation is known as the cumene process.

The cumene process has various drawbacks when the process is directly applied to a process for producing a methylphenol and ketone starting from an alkylbenzene having one secondary alkyl group and 1–3 methyl groups. When a methylbenzene having one secondary alkyl group and 1–3 methyl groups are oxidized, there are formed two or more hydroperoxides such as a tertiary hydroperoxide (hereinafter referred to as "3 - HPO") formed by oxidation of the tertiary carbon atoms of the secondary alkyl group and a primary hydroperoxide (herinafter referred to as "1 - HPO") formed by oxidation of the primary carbon atom of the methyl group directly attached to benzene nucleus, and therefore, the subsequent acid decomposition reaction becomes complicated.

The ratio of the resulting 3 - HPO to 1 - HPO varies depending upon the type of the secondary alkyl group of the alkylbenzene and number and position of the methyl groups directly attached to the benzene nucleus. For example, oxidation of 3,5-dimethylcumene gives about 70 molar parts of 3,5-dimethyl-α,α-dimethylbenzyl hydroperoxide (as 3 - HPO) and about 30 molar parts of 3-methyl-5-isopropylbenzyl hydroperoxide (as 1 - HPO).

As the result of the acid decomposition treatment, most of the 3 - HPO is acid-decomposed to form a methyl phenol and acetone, and small amount of 3 - HPO is converted to alcohols and other by-products. On the other hand, most of the 1 - HPO is acid-decomposed to form an alkylphenol having one secondary alkyl group and formaldehyde, and a small amount of 1 - HPO is converted to alcohols and other by-products. The acid decomposition reaction rate of 1 - HPO is far less than that of 3 - HPO and therefore, as the acid decomposition reaction proceeds the, 3 - HPO concentration decreases faster and finally the residual hydroperoxide is mostly 1 - HPO. In order to decompose the residual 1 - HPO, a severer reaction condition should be applied.

When an oxidation product solution containing 70 molar parts of 3 - HPO and 30 molar parts of 1 - HPO obtained by oxidation of 3,5-dimethylcumene was acid-decomposed to the hydroperoxide conversion of 90%, 99.0% by mole of the residual hydroperoxide was 1 - HPO, i.e. 3-methyl-5-isopropylbenzyl hydroperoxide.

Further, alcohols derived from 3 - HPO and 1 - HPO cause condensation reactions with 3 - HPO and/or 1 - HPO during the acid decomposition treatment to form diaralkyl peroxides. The resulting diaralkyl peroxides do not react any further under the usual acid decomposition conditions. An especially severe reaction condition is necessary to proceed the reaction further.

It is very difficult to recover the desired methylphenol by neutralizing the acid decomposition product solution obtained under usual conditions and containing residual hydroperoxides mainly composed of 1 - HPO and diaralkyl peroxides, and then distilling from the resultant solution. For example, when the acid decomposition product solution is heated, undesirable side reactions are caused by these peroxides to produce many by-products each having a boiling point close to that of the desirable methylphenol resulting in lower yield and purity of the methylphenol, and coloring thereof. Further the high content of the peroxides may result in an accidental explosion upon distillation. Therefore, for the purpose of facilitating the separation of the methylphenol by distillation, it is desirable to obtain an acid decomposition product solution containing as small an amount of the residual hydroperoxides as possible by sufficiently carrying out the acid composition reaction. However, when the acid decomposition treatment is conducted under severer conditions such as higher temperature and longer reaction time so as to reduce the content of residual hydroperoxides composed mainly of 1 - HPO and diaralkyl peroxide, condensation reaction of formaldehyde produced by the acid decomposition of 1 - HPO with the desired methylphenols is caused and high boiling point products are formed and, in addition, side reactions due to the peroxides occur so that the yield and/or the purity of the methylphenol are lowered.

For example, an oxidation product solution containing 70 molar parts of 3 - HPO and 30 molar parts of 1 - HPO obtained by oxidizing 3,5-dimethylcumene was acid-decomposed in solvent acetone in the presence of perchloric acid as a catalyst and the acid decomposition treatment was stopped when 84.96% of the hydroperoxide was decomposed. The resulting acid decomposition product solution was neutralized and analyzed by gas chromatography. An example of the chromatograms is shown in FIG. 1, which indicates that the neutralized solution contains six by-products as well as 3,5-xylenol and acetone. When the neutralized solution was distilled under reduced pressure in a batch-wise system by a packed tower of 20 theoretical plates, the separation of 3,5-xylenol from the X 4 component was very difficult because their boiling points are so close. In addition, thus obtained 3,5-xylenol was markedly colored and when the temperature of the still reaches 120° C., some components were thermally decomposed and the decomposition products contaminate the end product, 3,5-xylenol. Therefore, it was actually impossible to obtain 3,5-xylenol of high purity in good yield.

In view of the foregoing, in order to obtain the methylphenol of high purity in good yield, it is necessary to stop the acid decomposition reaction when the most amount of 3 - HPO is acid-decomposed and then to decompose the residual hydroperoxides mainly composed of 1 - HPO and diaralkyl peroxides present in the acid decomposition product solution by a certain means prior to the distillation. As a method for solving such problem, Japanese Patent Publication No. 45854/1974 discloses a process for producing both cresol and acetone by decomposing cymene hydroperoxide obtained by oxidizing cymene with molecular oxygen which comprises decomposing cymene hydroperoxide in the presence of an acid catalyst, stopping the decomposition reaction when the concentration of the hydroperoxide in the reaction product falls in 0.5-10% by weight, neutralizing the reaction product, decomposing the residual hydroperoxides by heating the product and then recovering cresol and acetone. According to the above mentioned process, however, relatively long treating period and high temperature are necessary to thermally decompose the diaralkyl peroxides present in the acid decomposition product solution to such an extent that an explosive accident in the later step, e.g. a separation step of the desired methylphenol, can be avoided. Further, these requirements will result in lowering the yield of the methylphenol and the selectivity thereto.

SUMMARY OF THE INVENTION

According to the present invention there is provided a process for preparing a methylphenol from an alkylbenzene which comprises oxidizing by molecular oxygen an alkylbenzene having one secondary alkyl group and 1-3 methyl groups of the general formula I

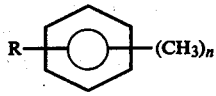
(I)

where R is a secondary alkyl group and n is an integer of 1-3, acid-decomposing the oxidation product solution in the presence of an acid catalyst, stopping the acid decomposition reaction before its completion, hydrogenating the acid decomposition product solution in the presence of a hydrogenation catalyst in the presence or absence of a solvent, and recovering the resulting methylphenol of the general formula (II)

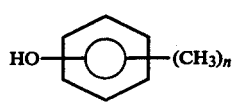
(II)

where n is an integer of 1-3 from the hydrogenation product solution.

An object of the present invention is to provide a process for preparing a methylphenol starting from an alkylbenzene in good yield.

Another object of the present invention is to provide a process for preparing economically a methylphenol of high purity starting from an alkylbenzene.

A further object of the present invention is to provide a process for preparing economically and safely a methylphenol of high purity starting from an alkylbenzene.

Figure 1:
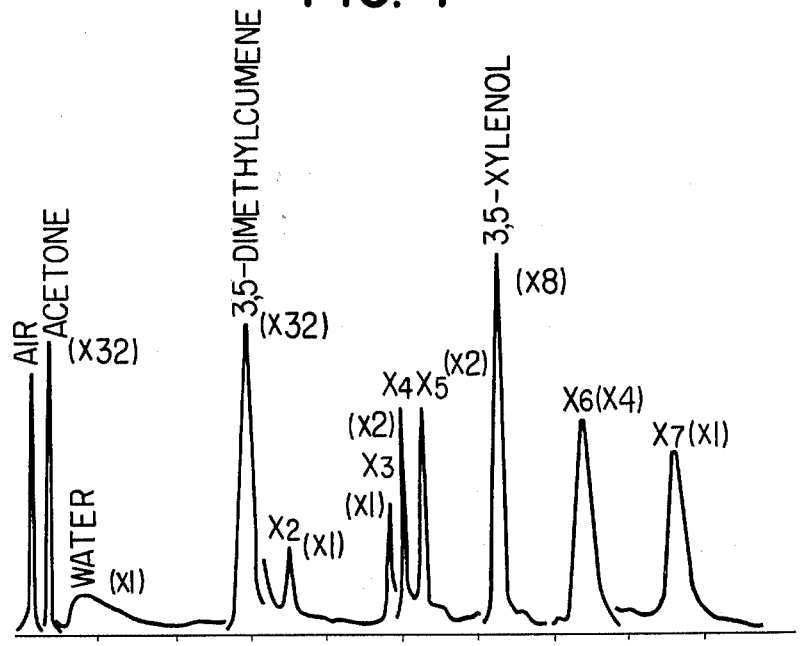
FIG. 1 shows an example of chromatograms of the acid decomposition product solution in Example 1.

The symbol, (x1), (x2), ..., (x64), given to each peak in the above figures, indicates that the height of the each peak is reduced to 1/1, ½, ..., 1/64 times the original height, respectively.

DESCRIPTION OF THE PREFERRED EMBODIMENTS

The alkylbenzene having one secondary alkyl group and 1-3 methyl groups in the present invention is a nuclear substituted benzene having one secondary alkyl group such as isopropyl, secondary butyl and the like and 1-3 methyl groups.

Typical examples of the said alkylbenzenes are o-cymene, m-cymene, p-cymene, 2,4-dimethylcumene, 3,4-dimethylcumene, 3,5-dimethylcumene, 2,4,6-trimethylcumene, and p-isobutyltoluene, preferred with 3,5-dimethylcumene.

The alkylbenzenes may be oxidized with a gas containing molecular oxygen such as oxygen gas and air and the like, according to a conventional oxidation procedure.

The oxidation product solution thus oxidized may be acid-decomposed under conventional conditions in the presence of a mineral acid such as sulfuric acid, perchloric acid and the like, or a mixture thereof.

The acid decomposition is stopped when the hydroperoxide conversion falls in the range of 84-90%. For the purpose of stopping the acid decomposition reaction, the acid catalyst is removed by contacting with an alkaline neutralizer, e.g. aqueous alkali, and an ion exchange resin, etc. At a hydroperoxide conversion of less than 84%, the yield of the end product, methylphenol, is low and, in addition, safety upon distillation is not assured. While, at a hydroperoxide conversion of more than 90% the yield and the purity of methylphenol are low, too.

What is meant by "hydroperoxide" in this invention is 3 - HPO and 1 - HPO.

As defined previously, 3 - HPO is a tertiary hydroperoxide as produced by oxidizing the tertiary carbon atom of the secondary alkyl group of the alkylbenzene having one secondary alkyl group and 1-3 methyl groups. An example of 3 - HPO is 3,5-dimethyl-α,α-dimethylbenzyl hydroperoxide of the formula III

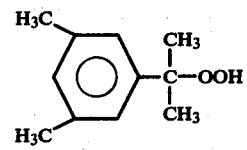
(III)

1 - HPO is a primary hydroperoxide as produced by oxidizing at least one primary carbon atom of 1-3 methyl groups directly attached to the benzene nucleus of the alkylbenzene having one secondary alkyl group and 1-3 methyl groups.

An example of 1 - HPO is 3-methyl-5-isopropylbenzyl hydroperoxide of the formula IV

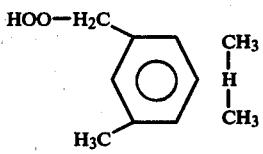
(IV)

The acid decomposition product solution neutralized as above is hydrogenation in the presence of a hydrogenating catalyst.

The hydrogenation catalyst used in the hydrogenation step may be that as used for conventional hydrogenation, for example, a metal belonging to the Group VIII of the Periodic Table such as iron, cobalt, nickel, ruthenium, rhodium, palladium, osmium, iridium, and platinum, and copper and chromium, and other metals having hydrogenation activity, and compositions thereof.

The metal or metal composition may be carried on a carrier such as activated carbon, alumina, silica, diatomaceous earth, asbestos, barium sulfate and the like. Ruthenium, rhodium, palladium and platinum are preferred.

The hydrogenation may be carried out in a one-step or two-step procedure in the present invention.

The temperature of the one-step hydrogenation is a temperature ranging from 50° C. to 200° C., preferably with from 80° C. to 150° C. At a temperature lower than 50° C., each rate of hydrogenation of the residual hydroperoxides mainly composed of 1 - HPO, diaralkyl peroxides and other by-products in the acid decomposition product solution is so low that the hydrogenation treatment is not practical. While at a temperature higher than 200° C. the yield of the methylphenol is lowered due to undesirable side reactions and there may happen an explosion accident in the hydrogenating step.

In the two-step procedure, the first hydrogenation step is carried out at a temperature ranging from 50° C. to 200° C. and the second hydrogenation step is carried out at a temperature higher than the temperature in the first hydrogenation step, higher than 50° C. and not higher than 350° C., preferred with from 150° C. to 340° C. Most amount of peroxides such as the hydroperoxide and the diaralkyl peroxide are decomposed in the first hydrogenation step and therefore, the second hydrogenation step can be effected at a temperature higher than that in the first hydrogenation step. When the temperature in the second hydrogenation step is not higher than 50° C., the rate of hydrogenation is so low that the second hydrogenation treatment is not practical. When the temperature is higher than 350° C., the amount of original alkylbenzene resulting from the by-products of the acid decomposition step decreases and the amount of the lower boiling point product resulting from the said by-products increases and the yield of the methylphenol lowers.

In the present invention, the pressure in the hydrogenation step is not critical and may be lower than atmospheric pressure or higher than 50 Kg./cm². (gauge), but in general 0–50 Kg./cm². (gauge) is commercially preferable.

The contact time of hydrogen in the hydrogenation step may be optionally selected depending upon the type of hydrogenation catalyst and the temperature of hydrogenation, etc. In general, it ranges from 0.2 to 10 hours. In a period shorter than 0.2 hour the hydrogenation reaction does not proceed sufficiently, while longer than 10 hours there occurs disadvantageously hydrogenation of the benzene nucleus.

After completion of the hydrogenation step, the end product, methylphenol, and the starting material, alkylbenzene having one secondary alkyl group and 1-3 methyl groups, may be recovered from the hydrogenation product solution by distillation.

The methylphenol obtained by the present invention is a methylphenol having one hydroxy group and 1-3 methyl groups directly attached to a benzene nucleus and may be represented by the general formula II

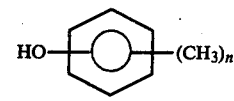

(II)

when n is an integer of 1-3.

Typical methylphenols are o-cresol, m-cresol, p-cresol, 2,4-xylenol, 3,4-xylenol, 3,5-xylenol and 2,4,6-trimethylphenol, etc.

The hydrogenation reaction in the present invention is considerably exothermic. Therefore, for the purpose of preventing overheating and explosion in the hydrogenation step and facilitating control of the temperature, the acid decomposition product solution may be preferably incorporated prior to the hydrogenation step with a solvent substantially inert and easily separable from the desired methylphenol by distillation such as benzene, alkylbenzenes, aliphatic alcohol, ether and the like.

The acid decomposition product solution contains the starting material, i.e. remaining alkylbenzene having one secondary alkyl group and 1-3 methyl groups, the end product, i.e. methylphenol, the residual hydroperoxide mainly composed of 1 - HPO, diaralkyl peroxides, and on occasion, a solvent as mentioned above.

When solvent is used, it is removed after the hydrogenation step in the one-step hydrogenation procedure and after completion of the first and or the second hydrogenation step in the two-step procedure.

The solvent and the starting material, alkylbenzene having one secondary alkyl group and 1-3 methyl groups, separated from the hydrogenation product solution can be used again as the solvent and the starting material, respectively after a simple washing treatment.

The process of the present invention may be carried out batch-wise, semi-continuously or continuously, and preferably semi-continuously or continuously.

According to the present invention, the residual hydroperoxides, diaralkyl peroxides and other by-products in the acid decomposition product solution can be decomposed and most of them can be converted to the original starting material, alkylbenzene, without any loss of the end product, methylphenol. Therefore, the present process is quite economical. When the hydrogenation is effected by the one-step procedure, highly pure methylphenol can be efficiently and safely produced in good yield and when the hydrogenation is effected by the two-step procedure, the purer methylphenol can be produced more efficiently.

The present invention will be described more in detail in the following examples. In the examples, symbols $X_0$–$X_7$ represent the components corresponding to the peaks in the chromatograms attached hereto. The yield is the yield of 3,5-xylenol based on the charged hydroperoxide in the hydrogenation step, and the selectivity is referred to 3,5-xylenol based on the consumed 3,5-dimethylcumene in the overall process.

However, these examples are intended to illustrate the invention and are not to be construed to limit the scope of the invention. Unless other wise specified, percents and parts are those by weight expecting conversions, yields and selectivities.

EXAMPLE 1

3,5-Dimethylcumene was oxidized with air and a portion of the remaining 3,5-dimethylcumene was distilled off from the oxidation product solution to obtain a starting liquid containing 38.45% of the hydroperoxides, which was subjected to continuous acid decomposition treatment by using perchloric acid as a catalyst in the following manner. In a reaction vessel fitted with a reflux condenser and a stirrer, 44.7 parts of the starting material liquid containing the hydroperoxides and 20.2 parts of a 0.06% acetone solution of perchloric acid were supplied, and the acid decomposition treatment was carried out by completely mixing the reactants under conditions such that the temperature was 45° C. and the contacting time 0.63 hour. The acid decomposition product solution was then drawn from the bottom of the reaction vessel and neutralized immediately.

The composition of the acid decomposition product solution thus obtained was acetone 36.31%, 3,5-dimethylcumene 40.09%, 3,5-xylenol 11.22%, hydroperoxides 4.00%, diaralkylperoxides 3.21% and other by-products 5.17%. The acid decomposition product solution was subjected to gas chromatography. The gas chromatogram thus obtained is shown in FIG. 1. Apparent from FIG. 1, the main by-products each having a boiling point higher than that of 3,5-dimethylcumene were $X_2$, $X_3$, $X_4$, $X_5$, $X_6$ and $X_7$. The conversion of hydroperoxides in the acid decomposition step was 84.96%.

The acid decomposition product solution was caused to pass through a fixed bed reaction pipe packed with alumina bearing 0.5% of palladium, together with hydrogen gas to carry out the first hydrogenation treatment under the condition that the temperature was 110° C., the pressure 0 kg./cm.$^2$ (gauge) and the contacting time 0.33 hour. The composition of the first hydrogenation product solution drawn from the bottom of the reaction pipe was acetone 36.29%, 3,5-dimethylcumene 41.27%, 3,5-xylenol 11.33%, hydroperoxides 0.01%, diaralkylperoxides 0.06% and other by-products 11.04%. The main by-products were $X_3$, $X_4$, $X_5$, $X_6$ and $X_7$ which were contained in the first hydrogenation product solution in amounts of 0.47%, 0.63%, 1.34%, 4.30% and 0.67%, respectively. 100% of $X_2$, 99.9% of hydroperoxides and 99.1% of diaralkylperoxides were decomposed by the first hydrogenation treatment.

The composition of the bottoms obtained by distilling off materials each having a lower boiling point such as acetone and the like from the first hydrogenation product solution was acetone 2.00%, 3,5-dimethylcumene 63.80%, 3,5-xylenol 17.51% and other by-products 16.69%.

The bottoms were equally divided. One half was distilled batch-wise under reduced pressure by means of a packed tower having 10 theoretical plates so that 3,5-xylenol having a purity of 94.9% was separated in an yield of 62.2% and a selectivity of 54.1%.

The other was further subjected to the second hydrogenation treatment by using alumina bearing 0.5% of palladium under the condition that the temperature was 190° C., the pressure 5 kg./cm.$^2$ (gauge) and the contacting time 1.12 hours.

Figure 2:
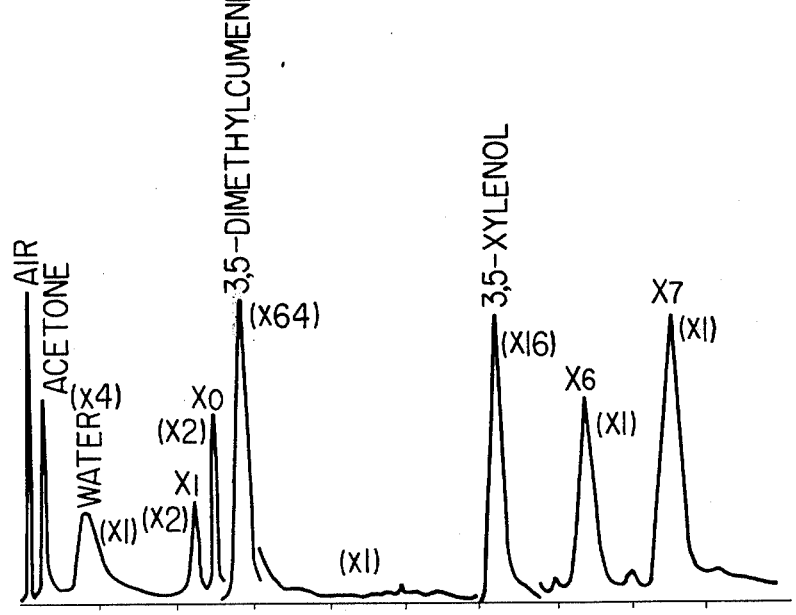
FIG. 2 shows an example of chromatograms of the first hydrogenation product solution in Example 1.

The composition of the second hydrogenation product solution was acetone 2.00%, 3,5-dimethylcumene 71.20%, 3,5-xylenol 17.51% and other by-products 9.29%. The second hydrogenation product solution was subjected to gas chromatography. The gas chromatogram thus obtained is shown in FIG. 2. As clearly shown in FIG. 2, the main by-products were $X_0$, $X_1$, $X_6$ and $X_7$ which were contained in the second hydrogenation product solution in amounts of 1.31%, 0.66%, 0.67% and 1.03%, respectively. As the result of the second hydrogenation treatment, 100% of each of $X_3$, $X_4$ and $X_5$ and 90.0% of $X_6$ were decomposed, and most amount thereof were converted to 3,5-dimethylcumene. On the other hand, the loss of 3,5-xylenol in the second hydrogenation step was hardly confirmed.

The second hydrogenation product solution was distilled batchwise under reduced pressure by using a packed tower having 10 theoretical plates so that 3,5-xylenol having a purity of not less than 99.5% was separated in an yield of 62.2% and a selectivity of 73.2%.

EXAMPLE 2

A similar acid decomposition treatment to that in Example 1 was repeated except that the concentration of the hydroperoxides contained in the starting material liquid was changed to 48.43% and 41.7 parts of the starting material liquid and 21.2 parts of the acetone solution of perchloric acid were supplied to the reaction vessel and further the contacting time was extended to 0.67 hour.

The composition of the acid decomposition product solution after neutralization was acetone 40.37%, 3,5-dimethylcumene 31.36%, 3,5-xylenol 13.20%, hydroperoxides 3.36%, diaralkylperoxides 3.94% and other by-products 7.77%. The main by-products each having a higher boiling point than 3,5-dimethylcumene were $X_2$, $X_3$, $X_4$, $X_5$, $X_6$ and $X_7$. The conversion of hydroperoxides in the acid decomposition step was 89.63%.

A similar treatment to the first hydrogenation treatment in Example 1 was repeated with respect to the above-mentioned acid decomposition product solution except that the temperature, pressure and contacting time were changed to 104° C., 5.0 kg./cm.$^2$ (gauge) and 0.78 hour, respectively. The composition of the first hydrogenation product solution thus obtained was acetone 40.35%, 3,5-dimethylcumene 34.66%, 3,5-xylenol 13.88%, hydroperoxides 0.02%, diaralkylperoxides 0.07% and other by-products 11.02%. The main by-products were $X_3$, $X_4$, $X_5$, $X_6$ and $X_7$ which were contained in the first hydrogenation product solution in amounts of 0.30%, 0.65%, 0.89%, 4.00% and 1.17%, respectively. As the result of the first hydrogenation treatment, 100% of $X_2$, 99.5% of hydroperoxides and 98.1% of diaralkylperoxides were decomposed.

The first hydrogenation product solution was equally divided. One half was distilled to remove acetone and then distilled under reduced pressure by a packed tower having 10 theoretical plates, and 3,5-xylenol having a purity of 94.0% was separated in an yield of 62.0% and a selectivity of 61.4%.

The other was subjected to the second hydrogenation treatment by using alumina bearing 0.5% of palladium under such a condition that the temperature was 183° C., the pressure 10.0 kg./cm.$^2$ (gauge) and the contacting time 0.78 hour, without distilling off the materials each having a lower boiling point such as acetone and the like.

The composition of the second hydrogenation product solution was acetone 38.71%, 3,5-dimethylcumene 38.95%, 3,5-xylenol 14.09% and other by-products 8.25%. The main by-products were $X_0$, $X_1$, $X_3$, $X_5$, $X_6$ and $X_7$ which were contained in the second hydrogenation product solution in amounts of 0.60%, 0.37%, 0.06%, 0.09%, 0.73% and 1.24%, respectively.

After distilling off all the materials having a lower boiling point such as acetone and the like from the second hydrogenation product solution, the resultant solution was distilled under reduced pressure by using a packed tower having 10 theroretical plates. As the result, 3,5-xylenol having a purity of not less than 99.5% was separated in an yield of 62.3% and a selectivity of 72.7%.

EXAMPLE 3

A similar procedure to that in Example 1 was repeated to prepare 3,5-xylenol except that in the first hydrogenation treatment, the catalyst, temperature and contacting time were changed to activated carbon, 100° C. and 1.00 hour, respectively, and in the second hydrogenation treatment, the catalyst, temperature and contacting time were changed to copper-chromium catalyst (the ratio by weight of copper/chromium: 49/51), 195° C. and 1.67 hours, respectively.

The composition of the first hydrogenation product solution after distilling off all the materials having a lower boiling point such as acetone and the like was acetone 0.80%, 3,5-dimethylcumene 64.77%, 3,5-xylenol 17.50%, hydroperoxides 0.05%, diaralkylperoxides 0.14% and other by-products 16.74%. While, the composition of the second hydrogenation product solution was acetone 0.08%, 3,5-dimethylcumene 73.10%, 3,5-xylenol 17.72% and other by-products 9.10%. 100% of each of the hydroperoxides and the diaralkylperoxides was decomposed in the second hydrogenation step.

3,5-xylenol having a purity of 94.9% was separated from the first hydrogenation product solution in an yield of 61.0% and a selectivity of 56.9%. Also, 3,5-xylenol having a purity of not less than 99.5% was separated from the second hydrogenation product solution in an yield of 61.6% and a selectivity of 73.5%.

EXAMPLE 4

A similar procedure to that in Example 1 was repeated to prepare 3,5-xylenol except that in the first hydrogenation treatment, the catalytic metal component, temperature, pressure and contacting time were changed to platinum, 50° C., 10.0 kg./cm.$^2$ (gauge) and 0.71 hour, respectively, and in the second hydrogenation treatment, the catalytic metal component, temperature and contacting time were also changed to rhodium, 150° C. and 1.52 hours, and further the second hydrogenation treatment was effected without distilling off the materials each having a lower boiling point such as acetone and the like from the first hydrogenation product solution.

The composition of the first hydrogenation product solution was acetone 36.51%, 3,5-dimethylcumene 40.85%, 3,5-xylenol 11.40%, hydroperoxides 0.12%, diaralkylperoxides 0.45% and other by-products 10.67%. While the composition of the second hydrogenation product solution was acetone 35.95%, 3,5-dimethylcumene 44.96%, 3,5-xylenol 11.45%, hydroperoxides 0.01%, diaralkylperoxides 0.08% and other by-products 7.55%.

3,5-Xylenol having a purity of 94.6% was separated from the first hydrogenation product solution in an yield of 62.2% and a selectivity of 56.9%. Also, 3,5-xylenol having a purity of not less than 99.5% was separated from the second hydrogenation product solution in an yield of 62.2% and a selectivity of 67.7%.

EXAMPLE 5

A similar procedure to that in Example 2 was repeated to prepare 3,5-xylenol except that in the first hydrogenation treatment, the catalytic metal component, temperature, pressure and contacting time were changed to rhodium, 130° C., 0 kg./cm.$^2$ (gauge) and 0.25 hour, respectively, and in the second hydrogenation treatment, the catalyst, temperature, pressure and contacting time were changed to a copper-chrominum (the ratio by weight of copper/chrominum: 49/51), 250° C., 3.0 kg./cm.$^2$ (gauge) and 0.50 hour, respectively, and further the second hydrogenation treatment was carried out after distilling off all the materials having a lower boiling point such as acetone and the like from the first hydrogenation product solution.

The composition of the first hydrogenation product solution was acetone 39.95%, 3,5-dimethylcumene 33.73%, 3,5-xylenol 12.43%, hydroperoxides 0.01%, diaralkylperoxides 0.05% and other by-products 13.83%. The composition of the second hydrogenation product solution was acetone 0.09%, 3,5-dimethylcumene 63.46%, 3,5-xylenol 20.71%, and other by-products 15.71%, and 100% of each of the hydroperoxides and the diaralkylperoxides was decomposed in the second hydrogenation step.

3,5-Xylenol having a purity of 93.2% was separated from the first hydrogenation product solution in the yield of 55.5% and a selectivity of 53.8%. Also, 3,5-xylenol having a purity of not less than 99.5% was separated from the second hydrogenation product solution in the yield of 54.9% and a selectivity of 61.8%.

EXAMPLE 6

A similar procedure to that in Example 5 was repeated to prepare 3,5-xylenol except that in the first hydrogenation treatment the catalytic metal component, temperature, contacting time were changed to platinum, 150° C. and 0.20 hour, respectively, and in the second hydrogenation treatment, the catalyst, temperature, pressure and contacting time were alumina bearing 0.5% of platinum, 210° C. 7.0 kg./cm$^2$. (gauge) and 1.18 hours, respectively.

The composition of the first hydrogenation product solution was acetone 39.77%, 3,5-dimethylcumene 35.90%, 3,5-xylenol 12.4%, hydroperoxides 0.01%, diaralkylperoxides 0.05% and other by-products 11.86%. The composition of the second hydrogenation product solution was acetone 0.74%, 3,5-dimethylcumene 67.37%, 3,5-xylenol 21.29% and other by-products 10.60%, and 100% of each of the hydroperoxides and the diaralkylperoxides were decomposed in the second hydrogenation step. 3,5-Xylenol having a purity of 94.7% was separated from the first hydrogenation product solution in an yield of 55.3% and a selectivity of 57.3%. Also, 3,5-xylenol having a purity of not less than 99.5% was separated from the second hydrogenation product solution in an yield of 54.3% and a selectivity of 63.9%.

EXAMPLE 7

A similar procedure to that in Example 2 was repeated to prepare 3,5-xylenol except that in the first hydrogenation treatment, the temperature, pressure and contacting time were changed to 110° C., 0 kg./cm.$^2$ (gauge) and 0.32 hour, respectively, and in the second hydrogenation treatment, the temperature, pressure and contacting time were changed to 335° C., 5.0 kg./cm$^2$ (gauge) and 1.09 hours, respectively, and further the second hydrogenation treatment was carried out after distilling off all the materials having a lower boiling point such as acetone and the like from the first hydrogenation product solution.

The composition of the first hydrogenation product solution after distilling off all the materials having a lower boiling point such as acetone and the like was acetone 0.47%, 3,5-dimethylcumene 51.02%, 3,5-xylenol 20.63%, hydroperoxides 0.01%, diaralkylperoxides 0.04% and other by-products 27.83%. The composition of the second hydrogenation product solution was acetone 0.48%, 3,5-dimethylcumene 60.56%, 3,5-xylenol 22.44% and other by-products 16.52%, and 100% of the hydroperoxides, 100% of the diaralkylperoxides and 41% of the by-products were decomposed in the second hydrogenation step.

3,5-Xylenol having a purity of 92.7% was separated from the first hydrogenation product solution in a yield of 49.0% and a selectivity of 46.6%. Also, 3,5-xylenol having a purity of not less than 99.5% was separated from the second hydrogenation product solution in an yield of 66.9% and a selectivity of 52.5%.

COMPARATIVE EXAMPLE 1

A similar acid decomposition product solution to that in Example 2 was subjected to one-step hydrogenation treatment without distilling off all the materials having a lower boiling point such as acetone and the like, by using alumina bearing 0.5% of palladium under the condition that the temperature was 210° C., pressure 8.0 kg./cm.² (gauge) and contacting time 1.33 hours. The composition of the hydrogenation product solution was acetone 37.62%, 3,5-dimethylcumene 38.44%, 3,5-xylenol 10.40% and other by-products 13.54% and 100% of each of the hydroperoxides and the diaralkylperoxides was decomposed in the hydrogenation step.

However, when the hydrogenation product solution was distilled batchwise under reduced pressure by using a packed tower having 10 theoretical plates after distilling off the materials each having a lower boiling point such as acetone and the like, 3,5-xylenol hving a purity of not less than 99.5% was separated in an yield of 46.7% and a selectivity of 54.8%.

COMPARATIVE EXAMPLE 2

A similar acid decomposition product solution to that in Example 1 was neutralized and caused to flow in a heated packed tower. The heating treatment was carried out at a predetermined temperature under a pressure of 0 kg./cm.² (gauge) for 0.33 hour to decompose both of the hydroperoxides and the diaralkylperoxides. 3,5-xylenol was separated from the resultant solution in a similar manner to in Example 1. The results are shown in the following table.

|  | 110° C. | 230° C. |
| --- | --- | --- |
| Conversion of hydroperoxides | 98.9% | 100% |
| Conversion of diaralkyl peroxides | 75.0 | 85.4 |
| Yield of 3,5-xylenol | 61.0 | 52.9 |
| Selectivity to 3,5-xylenol | 55.4 | 48.1 |

What we claim is:

1. A process for preparing a methylphenol from an alkylbenzene which comprises oxidizing in the liquid phase an alkylbenzene having one secondary alkyl group, one to three methyl groups, and the formula (I):

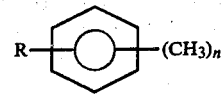

where R is a secondary alkyl group having from three to four carbon toms and n is an integer from one to three, inclusive, by contacting the alkylbenzene with molecular oxygen to provide an oxidation product solution containing tertiary hydroperoxide and primary hydroperoxide; acid-decomposing from 84 to 90 percent of the hydroperoxides in the presence of catalytic quantities of a mineral acid catalyst and terminating the acid decomposition by removing the acid catalyst with an alkali neutralizer or an ion-exchange resin when the aforesaid percentage of hydroperoxides is decomposed to provide a neutralized acid decomposition product; hydrogenating the acid decomposition product so obtained at a temperature of 50° to 200° C. under a pressure of 0 to 50 kg/cm³ (gauge) for 0.2 to ten hours in the presence of a hydrogenation catalyst which is copper, chromium or a metal from Group VIII of the Periodic Table of Elements to reduce the quantity of hydroperoxides; and recovering from the hydrogenation product methylphenol of the formula (II):

where n is as set forth above.

2. A process according to claim 1 in which R is isopropyl group.

3. A process according to claim 2 in which the alkylbenzene is at least one of o-cymene, m-cymene, p-cymene, 2,4-dimethylcumene, 3,4-dimethylcumene, 3,5-dimethylcumene and 4,5,6-trimethylcumene.

4. A process according to claim 3 in which the alkylbenzene is 3,5-dimethylcumene.

5. A process according to claim 1 in which R is a secondary butyl group.

6. A process according to claim 5 in which the alkylbenzene is p-isobutyltoluene.

7. A process according to claim 6 in which the molecular oxygen is oxygen gas or air.

8. A process according to claim 1 in which the alkaline neutralizer is an aqueous alkali.

9. A process according to claim 1 in which the hydrogenation is effected in one step at a temperature ranging from 50° C. to 200° C.

10. A process according to claim 1 in which the hydrogenation is effected in two steps, first at a temperature ranging from 50° C. to 200° C. and then at a temperature higher than the previous temperature and higher than 50° C. and not higher than 350° C.

11. A process according to claim 1 in which the metal belonging to the Group VIII of the Periodic Table is iron, cobalt, nickel, ruthenium, rhodium, palladium, osmium, iridium, or platinum.

12. A process according to claim 1 in which the catalyst is carried on activated carbon, alumina, silica, diatonaceous earth, asbestos or barium sulfate.

13. A process according to claim 1 in which the solvent is benzene, an aliphatic alcohol, an ether or an alkylbenzene.

14. A process according to claim 10 in which the molecular oxygen is air, the alkylbenzene is 3,5-dimethylcumene, the acid decomposition reaction is stopped when the hydroperoxide conversion falls in the range of 84–90% by removing the acid catalyst by contacting with an aqueous alkali, each hydrogenetion treatment is carried out under the pressure of 0–30 kg./cm.$^2$ (gauge) using acetone as solvent for 0.2–10 hours, and the hydrogenation catalyst is alumina or activated carbon each bearing ruthenium, rhodium, palladium, or platinum or copper-chromium.

* * * * *